(12) United States Patent
Hamamatsu et al.

(10) Patent No.: US 7,940,385 B2
(45) Date of Patent: May 10, 2011

(54) DEFECT INSPECTION APPARATUS AND ITS METHOD

(75) Inventors: Akira Hamamatsu, Yokohama (JP); Hisae Shibuya, Chigasaki (JP); Shunji Maeda, Yokohama (JP)

(73) Assignee: Hitachi High-Technologies Corporation, Tokyo (JP)

( * ) Notice: Subject to any disclaimer, the term of this patent is extended or adjusted under 35 U.S.C. 154(b) by 299 days.

(21) Appl. No.: 12/153,853

(22) Filed: May 27, 2008

(65) Prior Publication Data

US 2009/0027664 A1 Jan. 29, 2009

(30) Foreign Application Priority Data

Jul. 23, 2007 (JP) ................................ 2007-190300

(51) Int. Cl.
*G01N 21/88* (2006.01)
(52) U.S. Cl. ............... 356/237.5; 356/237.1; 356/237.4
(58) Field of Classification Search .... 356/237.1–237.6, 356/389–394; 250/559.42, 559.48
See application file for complete search history.

(56) References Cited

U.S. PATENT DOCUMENTS

| | | | | |
|---|---|---|---|---|
| 5,905,650 | A | * | 5/1999 | Tsutsui et al. ................. 700/110 |
| 6,009,545 | A | * | 12/1999 | Tsutsui et al. ................. 714/718 |
| 6,762,831 | B2 | * | 7/2004 | Shibata et al. ............. 356/237.2 |
| 6,855,930 | B2 | * | 2/2005 | Okuda et al. .................. 250/310 |
| 7,539,584 | B2 | * | 5/2009 | Bell et al. ......................... 702/81 |
| 2007/0182958 | A1 | * | 8/2007 | Manabe et al. ............ 356/237.2 |

FOREIGN PATENT DOCUMENTS

| | | | |
|---|---|---|---|
| JP | 58223328 | A * | 12/1983 |
| JP | 62-89336 | | 4/1987 |
| JP | 5-273110 | | 10/1993 |
| JP | 9-210919 | | 8/1997 |
| JP | 2002-181725 | | 6/2002 |
| JP | 2003-98111 | | 4/2003 |
| JP | 2004-53972 | | 2/2004 |
| JP | 2004-93252 | | 3/2004 |
| JP | 2007-24737 | | 2/2007 |

* cited by examiner

*Primary Examiner* — Sang Nguyen
(74) *Attorney, Agent, or Firm* — Antonelli, Terry, Stout & Kraus, LLP.

(57) ABSTRACT

In a defect inspection apparatus for performing an inspection with an optical system, the dimension of a defect is measured substantially concurrently with detection of the defect. In order to promote the accuracy of measurement of the defect dimension, a correction unit is provided which corrects the defect dimension by using a standard sample such as a standard particle.

10 Claims, 15 Drawing Sheets

801

811

| 0 | 0 | 0 | 0 | 0 | 0 | 0 | 0 | 0 |
|---|---|---|---|---|---|---|---|---|
| 0 | 0 | 0 | 0 | 0 | 0 | 0 | 0 | 0 |
| 0 | 0 | 0 | 0 | 10 | 0 | 0 | 0 | 0 |
| 0 | 0 | 0 | 18 | 45 | 23 | 0 | 0 | 0 |
| 0 | 0 | 3 | 24 | 250 | 59 | 17 | 0 | 0 |
| 0 | 0 | 0 | 4 | 33 | 30 | 6 | 0 | 0 |
| 0 | 0 | 0 | 0 | 5 | 0 | 0 | 0 | 0 |
| 0 | 0 | 0 | 0 | 0 | 0 | 0 | 0 | 0 |
| 0 | 0 | 0 | 0 | 0 | 0 | 0 | 0 | 0 |

| 2 | 2 | 2 | 3 | 3 | 5 | 4 | 1 | 4 |
|---|---|---|---|---|---|---|---|---|
| 1 | 1 | 3 | 4 | 1 | 4 | 4 | 2 | 4 |
| 3 | 2 | 3 | 1 | 13 | 4 | 4 | 4 | 3 |
| 5 | 2 | 1 | 15 | 47 | 28 | 2 | 3 | 4 |
| 4 | 1 | 7 | 27 | 252 | 62 | 20 | 1 | 2 |
| 2 | 3 | 5 | 8 | 36 | 32 | 10 | 1 | 1 |
| 4 | 1 | 4 | 5 | 10 | 4 | 2 | 5 | 4 |
| 5 | 5 | 3 | 5 | 2 | 2 | 1 | 3 | 3 |
| 2 | 3 | 1 | 4 | 1 | 3 | 5 | 3 | 1 |

DEFECT INSPECTION APPARATUS AND ITS METHOD

INCORPORATION BY REFERENCE

The present application claims priority from Japanese application JP2007-190300 filed on Jul. 23, 2007, the content of which is hereby incorporated by reference into this application.

BACKGROUND OF THE INVENTION

The present invention relates to a defect detection method and its apparatus in which when detecting defects present on a thin film substrate, a semiconductor substrate, a photo-mask and the like that are used for manufacturing a semiconductor chip, a liquid crystal product, a magnetic disk head and a sensor such as CCD or CMOS as well and then when analyzing the cause of the faults, the results of inspection can be displayed or outputted in a format easy for a user to analyze, thus permitting the cause of the faults to be surveyed.

Conventionally, the technique of detecting defects on, for example, a semiconductor substrate by using an optical measurement means has been known widely. For example, Patent Document 1 (JP-A-62-89336) discloses a technique in which rays of scattering light, generated from a defect under irradiation of a laser beam on a semiconductor substrate in the event that the defect is deposited thereon, are detected and a result of detection is compared with a result of an inspection of the same kind of semiconductor substrate executed immediately precedently, thereby making it possible to inspect the defect.

Also, Patent Document 2 (JP-A-5-273110) or patent Document 3 (JP-A-2003-98111) discloses a method in which a laser beam is irradiated on an object to be inspected and scattering rays of light generated from a particle or crystal defect of the inspected object are received and subjected to image processing to thereby measure a size of the particle or crystal defect.

On the other hand, in the production line of semiconductor substrate, thin film substrate and the like, a control method of monitoring defects on a substrate has hitherto been employed as one of methods for controlling the production process of products. In one of the monitoring methods, the surface of a substrate is inspected using a defect inspection apparatus and the lapse of the number of detected defects delivered out of the defect inspection apparatus is monitored so that a fault analysis of defects may be executed especially for a substrate for which the number of detected defects is large.

SUMMARY OF THE INVENTION

In the conventional process control method, rays of scattering light given off from a particle or a defect can be detected with an inspection apparatus of the light scattering type, used as the inspection apparatus for monitoring the production line, and they can be subjected to an image processing so as to calculate the dimension of the defect but there still remains a problem of failure to properly calculate the dimension.

The present invention contemplates solving the problem the conventional technique encounters and it is an object of this invention to provide a defect inspection method and its apparatus according to which when inspecting the procedures for producing a semiconductor wafer or a thin film substrate and conducting a fault analysis, a means for correcting the dimension is provided to thereby ensure that the defect dimension can be calculated properly and countermeasures against faults can be taken speedily.

Of inventions disclosed in the present application, typical ones will be outlined briefly as follows:

(1) A defect inspection apparatus for inspecting defects on an object to be inspected, comprises illumination means for irradiating a beam of light on the inspecting object, photo-detection means for detecting rays of light given off from the inspecting object under the irradiation of the light beam by the illumination means, defect detection means for detecting a defect by processing a signal obtained through detection by the photo-detection means, correction means for correcting the size of the detected defect by using a ratio between a quantity characteristic of the defect detected by the defect detection means and a corresponding characteristic quantity of a standard particle measured and calculated in advance, and display means for displaying the defect size corrected by the correction means.

(2) A defect inspection apparatus as recited in (1), wherein the photo-detection means has a sampling pitch which is half or less the optical resolution.

(3) A defect inspection method for detecting defects on an object to be inspected, comprises illumination step of irradiating a beam of light on the inspecting object, photo-detection step of detecting rays of light given off from the inspecting object under the irradiation of the light beam in the illumination step, defect detection step of detecting a defect by processing a signal obtained through detection in the photo-detection step, and correction step of correcting the size of the detected defect by using a ratio between a quantity characteristic of the defect detected in the defect detection step and a corresponding characteristic quantity of a standard particle measured and calculated in advance.

(4) A defect inspection method as recited in (3), wherein the photo-detection step is executed at a sampling pitch which is half or less the optical resolution.

These and other objects, features and advantages of the invention will be apparent from the following more particular description of preferred embodiments of the invention, as illustrated in the accompanying drawings.

DESCRIPTION OF THE EMBODIMENTS

Figure 1:
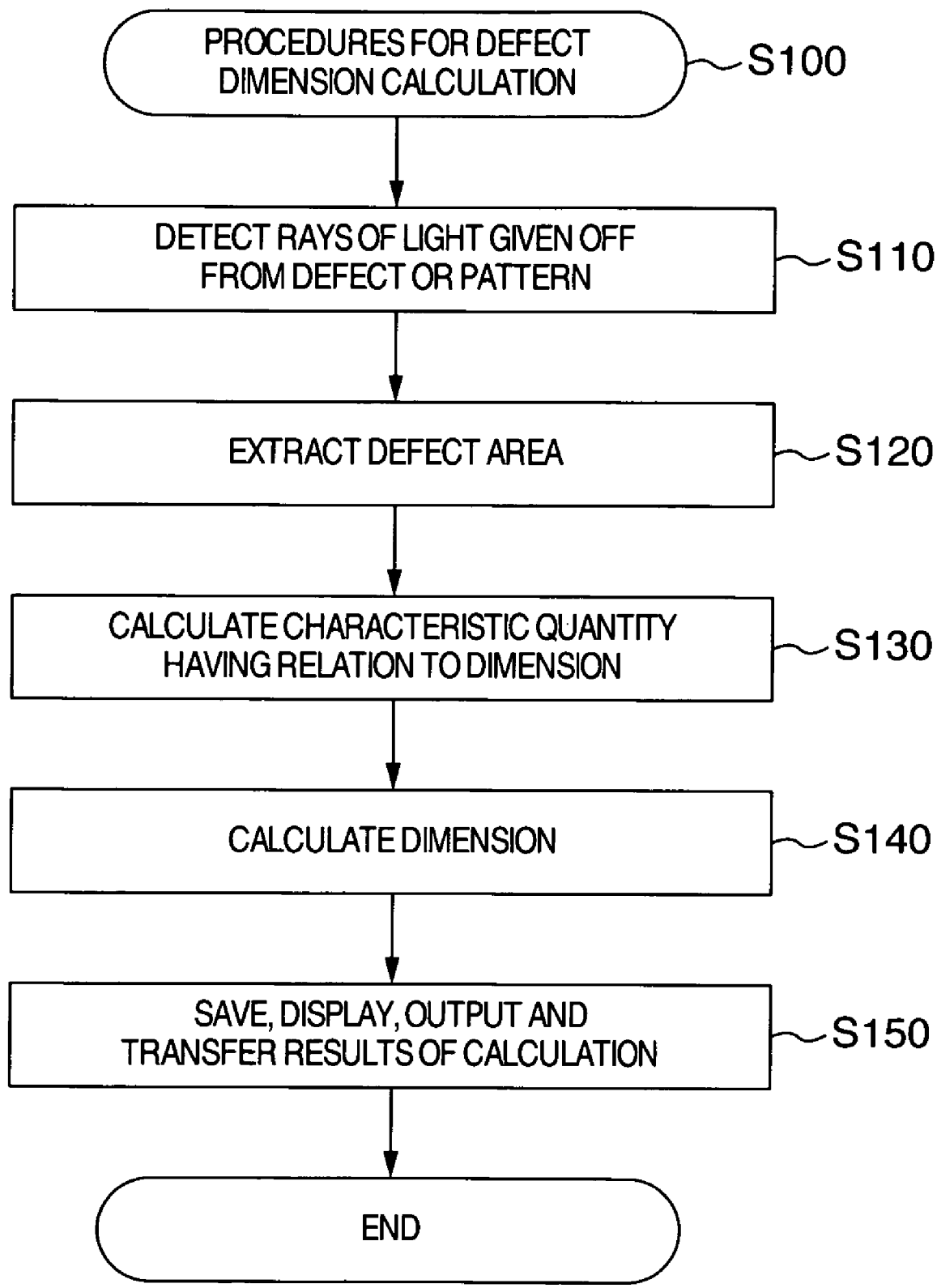
FIG. 1 is a flowchart showing procedures for defect dimension calculation according to the present invention.

Referring first to FIG. 1, the basic procedures for calculation of the size of a defect will be described.

Firstly, a beam of light is irradiated on an object to be inspected and rays of light (an electromagnetic wave) from a defect or pattern within an irradiated area are detected (step 110) and information about a component of detected rays of light which is based on the detected defect is extracted (step 120). Subsequently, of the thus obtained defect component information, a characteristic quantity (the sum or maximum value of signal intensities to be detailed later) related to a size of the defect is calculated (step 130). Then, out of the defect component information, the defect size calculated from the quantity of rays of scattering light is corrected by using a ratio between the now calculated characteristic quantity and a corresponding characteristic quantity of a standard particle measured and calculated in advance, thereby calculating a proper defect dimension (step 140). The result of calculated dimension is saved, displayed, outputted and transferred (step 150).

Namely, according to the present invention, the measurement result of the size of a defect can be corrected by using the comparative data between a characteristic quantity having the relation to the dimension of the defect and a corresponding characteristic quantity of a standard particle and consequently, a proper defect dimension can be calculated.

Details of the construction of a defect inspection apparatus and defect inspection system and a method of correcting the size of a defect, which are adapted for realizing the above advantage of the invention, will be described. An embodiment to be given hereinafter will be described as applied particularly to an example where defects on a semiconductor wafer are inspected but this is not limitative and the present invention can also be applied to a thin film substrate, a photo-mask, a TFT, a PDP and the like.

[Construction and Operation of Defect Inspection Apparatus and Defect Inspection System]

Figure 2:
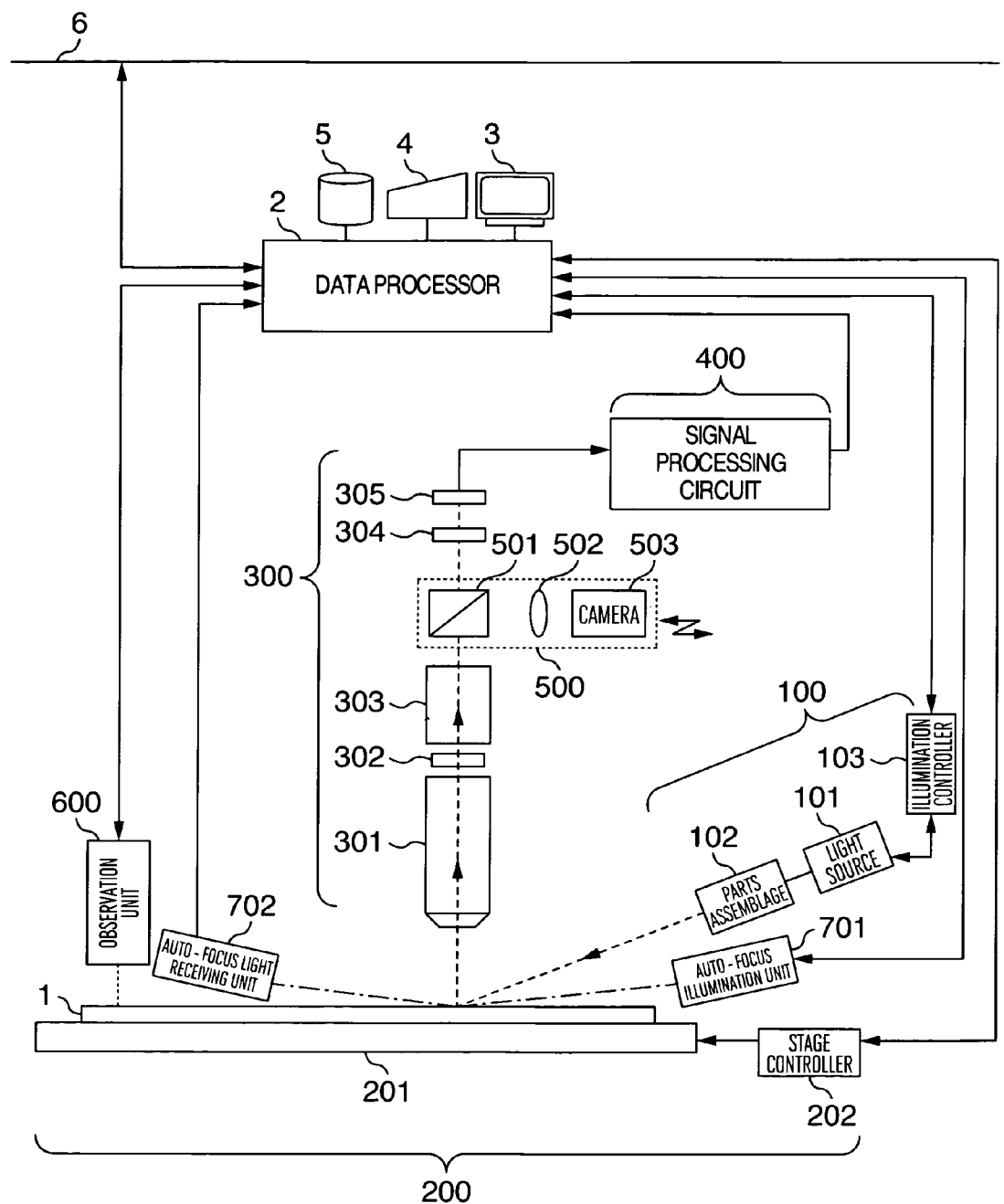
FIG. 2 is a block diagram showing the schematic construction of a defect inspection apparatus according to the present invention.

Turning to FIG. 2, an example of the defect inspection apparatus of this invention will be described. The defect inspection apparatus comprises an illumination optical system 100 for irradiating a beam of light on an object to be inspected 1, a stage unit 200 for holding the inspecting object 1, a photo-detection unit 300 for detecting rays of reflection light or scattering light given off from the inspecting object 1 under the irradiation of the light beam on the inspecting object 1, a signal processing circuit 400 for processing a signal as a result of photoelectric conversion of the detected rays of light and a data processor 2, additionally comprising as necessary a Fourier transform plane observing unit 500 adapted to pick up an image on a Fourier transform plane of the detection optical system and observe it, an observation unit 600 adapted to observe an alignment mark, for example, built on the inspecting object 1 for the purpose of positioning or position matching a detected defect or a pattern formed on the inspecting object 1, and an auto-focus illumination unit 701 and auto-focus light receiving unit 702 which is adapted to controllably locate the stage to a suitable focal position.

Defect detection with the present defect inspection apparatus is carried out in accordance with the procedures as below. A beam of light is irradiated on the inspecting object 1 carried on the stage unit 200 by means of the illumination optical system 100 and rays of reflection light or scattering light given off from the inspecting object 1 are collected and detected by the photo-detection unit 300. The illumination optical system 100 referred to herein includes a light source 101, an optical parts assemblage 102 and an illumination controller 103, the illumination controller 103 being operative to respond to a command from data processor 2 which is applied thereto from a an input unit 4 or by way of a network 6 so as to adjust the output of the light source 101. As the light source 101, a laser light source, for example, to be described later can appropriately selectively used as necessary. The illumination light beam is suitably shaped by means of the optical parts assemblage 102 so as to take a circular or linear form on the inspecting object 1. It will be appreciated that the illumination light beam may be either a parallel beam or non-parallel beam and if the quantity of light per unit area on the inspecting object 1 is desired to be increased, the illumination light may be irradiated at a high numerical aperture so as to be focused on the inspecting object or the output of the illumination light source may be increased.

Also, the stage unit 200 includes a stage 201 and a stage controller 202 so that the inspecting object 1 may be moved in the horizontal direction by means of the stage 201 and besides, with the help of the auto-focus illumination unit 701 and auto-focus light receiving unit 702, the stage 201 may be moved in the vertical direction so as to be brought into the focal position of the photo-detection unit 300, thus ensuring that detection of defects and measurement of their sizes can be executed over the entire area of the inspecting object 1. Then, the detection result is displayed on a data display unit 3 or transferred through the network 6.

The photo-detection unit 300 includes an objective lens 301, a spatial filter 302, an image forming lens 303, a polarization plate 304 and a sensor 305 as necessary. The optical lens is so structured as to focus rays of light from the inspecting object 1, out of the light beam irradiated by means of the illumination optical system 100, on the sensor 305. Further, the photo-detection unit 300 is so structured as to apply to rays of scattering light an optical process, for example, change/adjustment of optical characteristics by means of the spatial filter 302 and polarization plate 304. More specifically, since the spatial filter 302 shields a diffraction light pattern caused by diffraction light from a repetitive pattern of the inspecting object 1, it is disposed on the Fourier transform plane of the objective lens 301. The Fourier transform plane observing unit 500 so structured as to get to or get away from the optical path in the photo-detection unit 300 observes a diffraction pattern of the inspecting object 1 and the light shielding shape of the spatial filter 302 is set such that the observed diffraction pattern can be shielded. Namely, with the spatial filter 302 removed, the Fourier transform plane observing unit 500 is first inserted to the optical path of photo-detection unit 300, the optical path is caused to branch by means of a beam splitter 501 to permit an image of the Fourier transform plane of objective lens 301 to be picked up and observed by a camera 503 through the medium of a lens 502. The light shielding pattern of spatial filter 302 can be set in respect of individual kinds of the inspecting object 1 and individual production steps. Alternatively, the light shielding pattern of spatial filter 302 may remain unchanged during scanning or may be changed by using liquid crystal, for example, on real time base in accordance with areas undergoing scanning. In the case of using the spatial filter, the performance of detection of defects can be more improved with a parallel light beam used as the illumination light.

The polarization plate 304 may be used for optical processing as will be described below. Since the defect makes polarization of illumination liable to be random whereas the polarization state is prone to be conserved in an area where the pattern of the inspecting object 1 is normal or any pattern does not exist, rays of light from a defect can be detected highly efficiently by setting during detection the polarization plate in a direction in which P-polarization can transmit when S-polarization light is irradiated. In the case of irradiation of P-polarization light, the polarization plate may be set in a direction in which S-polarization light transmits.

Rays of light acquired by the photo-detection unit 300 as described above are subjected to photoelectric conversion and sent to the signal processing circuit 400 so as to be processed thereby, permitting the defect to be detected. The signal processing circuit 400 includes a section for detection of a defect and a section for measurement of the size of the defect. In detecting a defect, an input signal is binary-digitized, for example, and a signal in excess of a binary-digitized threshold value is determined as representing the defect and is outputted. The process of measurement of the defect size will be described later.

The present defect inspection apparatus further comprises the data display unit 3, input unit 4 and data storage 5 which are coupled to the data processor 2, so that an inspection can be executed while setting an arbitrary condition and then the inspection result and the inspection condition as well can be saved and displayed. The present defect inspection apparatus can also be coupled to the network 6 and can be allowed to share on the network 6 the inspection result, the layout information, lot number, inspection condition of the inspecting object 1 or data representative of an image of a defect observed by the observation unit and the kind of defect.

A description of details of the construction of the defect inspection apparatus according to the present invention and constituents appropriately additionally provided therefor will be supplemented.

As the light source 101, either a laser light source such as an Ar laser, a semiconductor laser, a YAG laser and a UV laser or a white light source such as a Xe lamp and a Hg lamp may be used. Especially when the sensitivity to detection of defects is desired to be promoted, the use of a light source having a short wavelength as the illumination light source is preferable and in this respect, the YAG laser, Ar laser and UV laser are suitable. Further, for a compact and inexpensive inspection apparatus, the semiconductor laser is recommendable. Furthermore, with a view to reducing an interference attributable to a light transmission type thin film formed on the inspecting object, the white light source or laser illumination having the capability to reduce the interference is suitable as the illumination light source. Then, for the aforementioned optical parts assemblage 102, a beam expander, a collimator lens or a cylindrical lens may be used purposefully.

The sensor 305 is used for receiving collected rays of light and applying them with photoelectric conversion and as this sensor, a TV camera, a CCD linear sensor, a TDI sensor, an anti blooming TDI or a photomultiplier, for example, may be employed. Especially, for detection of a slight quantity of light, the photomultiplier may preferably be used and for fast acquisition of a two-dimensional image, the TV camera may be recommendable. Further, in the case of the photo-detection system 300 being an image forming system, any one of the TV camera, CCD linear sensor, TDI sensor and anti-blooming TDI sensor may be preferable and in the case of the photo-detection system 300 being a focusing system, the photomultiplier may be preferable. In addition, if the dynamic range of rays of light received by the sensor 305 is large, that is, if rays of light having intensity for which the sensor is saturated are incident, a sensor added with the anti-blooming function may be recommended.

The auto-focus illumination unit 701 enables a light beam emitted from, for example, a white light source such as Hg lamp or a laser light source of He—Ne, for instance, to be irradiated on the inspecting object 1. If the wavelength of the light source used for the auto-focus illumination unit 701 is different from that of the light source used for the illumination optical system 100, noise in the light beam used for defect detection can be reduced.

The auto-focus light receiving unit 702 is adapted to receive a light component reflected from the inspecting object 1 out of the light beam emitted from the auto-focus illumination unit 701 and is implemented by a unit such as for example a position sensor which can detect the position of the light component. In addition, information acquired by the auto-focus light receiving unit 702 is sent to the stage controller 202 directly or through the medium of the data processor 2 and used for controlling the stage.

In the defect inspection apparatus shown in FIG. 2, the illumination optical system 100 is exemplified as illuminating the inspecting object 1 in one direction but alternatively, two or more illumination optical systems may be provided having different azimuths or different elevation angles or having them in combination to carry out inspection.

Figure 3:
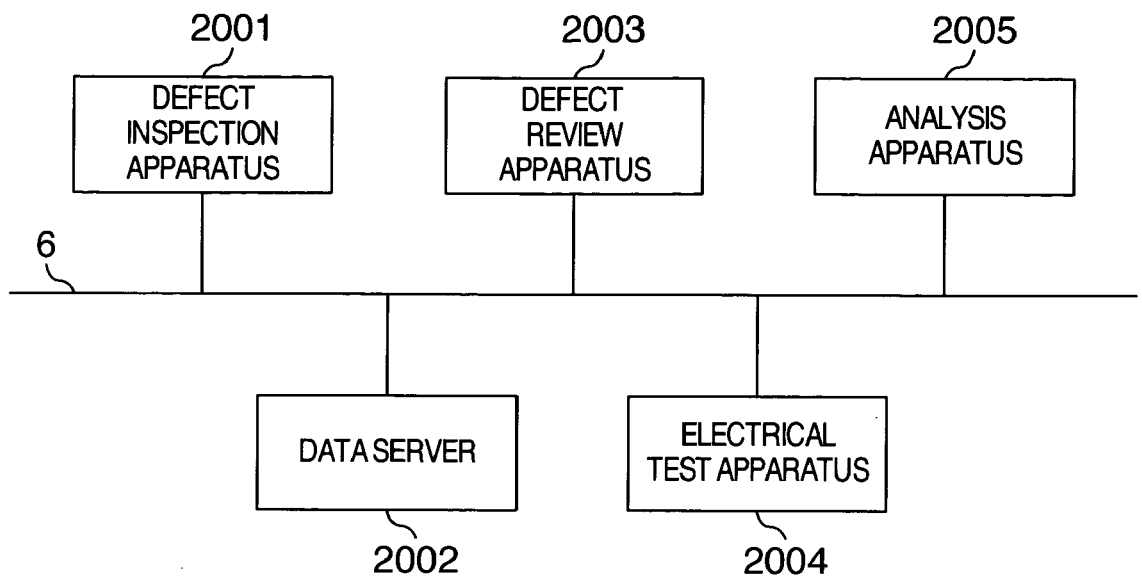
FIG. 3 is a block diagram for explaining the mode when the defect inspection apparatus according to the invention is operated as a system.

Next, the system configuration of the defect inspection apparatus of the present invention and its operation will be described. Reference will be made to FIG. 3 showing a block diagram useful to explain the defect inspection apparatus of the invention operating as a system.

The system comprises the defect inspection apparatus 2001 of the invention, a data server 2002, a defect review apparatus 2003, an electrical test apparatus 2004, an analysis apparatus 2005 and a network 6 to which individual apparatus are coupled. For example, the defect review apparatus 2003 is an SEM, the electrical test apparatus 2004 is a tester and the analysis apparatus 2005 is an apparatus for analyzing components of a defect, such as EDX. The data server 2002 is a computer capable of collecting and storing the inspection data of defect inspection apparatus 2001, the reviewing results of defect review apparatus 2003, the test results of electrical test apparatus 2004 and the analysis results of analysis apparatus 2005, and the network 6 is a communication network complying with, for example, Ethernet (trademark).

Next, operation of the system using the defect inspection apparatus of this invention will be described. After an inspection by the defect inspection apparatus 2001 has been executed, a defect for which countermeasures are to be taken is selected. A result of the inspection by the defect inspection apparatus 2001, including a serial number of the detected defect during inspection, position information of the defect and size information of the defect, is added with information about the selected defect and is then transmitted to the data server 2002 via the network 6. In a method of adding the information about the selected defect, a flag as to whether countermeasures are necessary, for example, may be added to the inspection result. Then, in order to investigate in greater detail the defect detected by the defect inspection apparatus 2001, the inspecting object is moved to the defect review apparatus 2003. For this movement, the inspecting object may be conveyed manually or mechanically. After completion of movement of the inspecting object to the defect review apparatus 2003, the defect review apparatus 2003 accesses the data server 2002 via the network 6 and receives the inspection result from the data server 2002, starting reviewing by using this inspection result. At that time, by consulting the information added by the defect inspection apparatus 2001 to preferentially review a defect needing countermeasures, the defect responsible for a cause of fault can be analyzed speedily. Similarly, by consulting the information added by the defect inspection apparatus 2001, the analysis apparatus 2005 can also analyze preferentially the defect needing countermeasures, thus enabling the cause of fault to be analyzed speedily.

These review data and analysis result are stored in the data server 2002 and are then corrected with the test result by the electrical test apparatus 2004 to finally decide the defect as to whether to be faulty or not. If the defect is not determined faulty finally, the data server 2002 transmits to the defect inspection apparatus 2001 the data for changing the standards adapted for selection of the defect against which countermeasures need to be taken and the standards for necessity/non-necessity of countermeasures against the defect in the inspection apparatus 2001 can be changed, so that the defect needing countermeasures can be selected with higher accuracies and countermeasures against faulty in the process of semiconductor production can be taken speedily.

The foregoing description has been given by way of example of transmission and reception of data through the network but the intervention of the network is not always necessary and the delivery of the data by means of a removable storage medium or a printed-out sheet of paper may be available.

Figure 4:
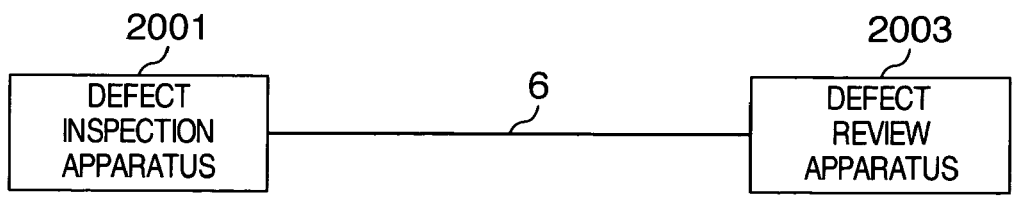
FIG. 4 is a block diagram for explaining the mode when the defect inspection apparatus according to the invention is used in combination with a defect review apparatus so as to operate as a system.

Further, the defect inspection apparatus 2001 according to the invention may be used in combination with the defect review apparatus 2003 in a different way as will be described below. Part of illustration of FIG. 3 is extracted therefrom as indicated in FIG. 4. In FIG. 4, an inspection apparatus designated at 2001 is the defect inspection apparatus according to the present invention, for example. Designated by 2003 is an apparatus for reviewing defects on the inspecting object, being implemented by a critical dimension SEM, for example. A network 6 is adapted for transmission and reception of data between the inspection apparatus 2001 and defect review apparatus 2003, establishing a system coupled by, for example, Ethernet (trademark). Operation will be described hereunder by taking a defect, for instance.

Firstly, defects on an inspecting object are inspected by means of the defect inspection apparatus 2001. A result of the inspection, including, for example, a serial number of a detected defect during inspection, position information of the defect and size information of the defect, is added to inspection data which in turn is transmitted to the defect review apparatus 2003 via the network 6. The inspecting object is moved to the defect review apparatus 2003, followed by defect reviewing work with the help of the defect review apparatus 2003. At that time, the magnification at the time of reviewing by the defect review apparatus 2003 is changed in compliance with the information about the size of the defect measured by the inspection apparatus 2001, making it possible to perform reviewing highly efficiently. More specifically, when the information about the size of the defect obtained from the inspection apparatus 2001 indicates a small defect, reviewing is executed at a high magnification during review so that details of the small defect may be observed quickly. Conversely, when the information about the size of the defect indicates a large defect, reviewing is executed at a low magnification during review so that the defect will not swell out of the review screen even for the large defect, enabling review to proceed and an entire image of the defect to be observed quickly. For example, when the size of a defect in inspection data transmitted from the inspection apparatus 2001 is 0.1 reviewing is executed by setting the review magnification in the defect review apparatus 2003 such that the field of view is 1 μm and if the size of a defect is 10 μm, reviewing is executed by setting the review magnification in the defect review apparatus 2003 such that the field of view is 100 μm. In this manner, highly efficient review covering small to large defects can be carried out to accomplish high-speed analysis of detected defects.

The present example has been described by way of example of delivering the information about the size of a defect from the inspection apparatus 2001 and changing the magnification of the review apparatus in accordance with the size but in an alternative, the information about review magnification and review view field in the defect review apparatus 2003 may be added to the inspection data by the inspection apparatus 2001. Also, in the present example, the defect review apparatus 2003 has been described as performing reviewing at a review magnification which makes the view field as large as ten times the size of a defect but this value of magnification may be changed to a different one and besides, if the accuracy of defect position information in the inspection apparatus 2001 is known, reviewing may be carried out at a magnification taking the magnification based on the defect size information and the accuracy of position information as well into account. In the present example, the review apparatus has been described as being a critical dimension SEM but alternatively, a review SEM or an optical type microscope system may be employed and the present method can be applied to apparatus or function purposing review.

Further, in the present example, reviewing of a defect with the help of the defect review apparatus 2003 has been described but even in the case that reviewing of a defect is executed by means of the defect inspection apparatus of the present invention, the present method can be applicable.

[Measurement of Size of Defect]

Next, a process of measuring the size of a defect with the defect inspection apparatus of the invention will be described. In measurement of dimensions of defects in the present invention, a measurement method using rays of scattering light from a defect is available. The size (particle diameter) of a defect particle and the magnitude of rays of scattering light from the particle can be approximated or analyzed appropriately through a known method based on "a correlation between the particle size and the illumination light wavelength" and the method will be explained below briefly.

When the particle diameter is far larger than the illumination light wavelength, it can be expressed using the Fraunhofer approximation. If the particle diameter is nearly three times the wavelength, the Lorenz Mie theory can be applied. If the particle diameter is smaller than the wavelength, the Rayleigh scattering theory can be applied. According to the Rayleigh scattering theory, the quantity of scattering light by a particle smaller than the wavelength of illumination light is a function of the particle diameter, the illumination wavelength and the refractive index and a Rayleigh scattering coefficient σ representing the index of scattering efficiency is expressed by the following equation:

$$\sigma = \frac{2\pi^5}{3} \cdot \frac{d^6}{\lambda^4} \left(\frac{n^2-1}{n^2+1}\right)^2$$

where π represents circle ratio, d particle diameter, λ wavelength and n refractive index of the particle. It will be seen from the Rayleigh scattering coefficient that when the illumination light wavelength is constant, the quantity of scattering light is proportional to the sixth power of the particle diameter. Accordingly, if the quantity of scattering light by the particle can be measured, a numerical value proportional to the particle diameter can be calculated. In other words, by multiplying the scattering light quantity by a suitable coefficient in terms of scalar, the particle diameter can be calculated. The above equation gives the index of scattering efficiency when the particle is in the air but the scattering efficiency on a wafer has substantially the same relation.

Figure 5A:
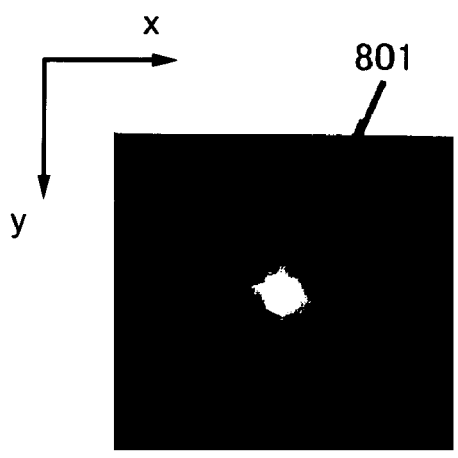
FIG. 5A is a diagram showing an image data when a defect is present.
Figure 5B:
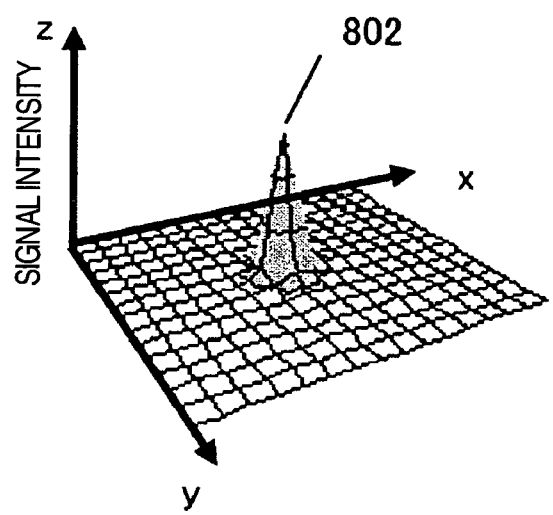
FIG. 5B is a diagram showing a distribution of signal intensities when defect data is measured.

Image data in the presence of a defect is illustrated in FIG. 5A and a distribution of signal intensities obtained when defect data is measured is illustrated in FIG. 5B. The two kinds of distribution of signal intensities are illustrated in a comparative fashion in FIGS. 6A and 6C and acquisition of maximum values of the signal intensities are illustratively shown in FIGS. 6B and 6D.

An image processed by the signal processing circuit 400 in the presence of a defect is exemplified as shown in FIG. 5A, demonstrating that defect data 801 exists in the center of the image. The defect data 801 is outputted from the sensor 305 and acquired in the form of data having a variable-density value by the signal processing circuit 400. The data in FIG. 5A is expressed three-dimensionally in FIG. 5B, indicating that x and y axes are coordinate axes for determining positions inside the image and signal intensities at the positions are plotted on z axis and that individual z-coordinate points are interconnected by curves. In FIG. 5B, a waveform 802 shows the defect data 801 in terms of waveform data. The waveform 802 has a sampling frequency corresponding to a sampling pitch of the photo-detection unit and for example, when the photo-detection unit 300 is comprised of an image forming optical system, the higher the magnification of the optical system and the smaller the size of one pixel of the sensor 305, the sampling frequency becomes higher. In the case of the photo-detection unit being a focusing optical system, the smaller the spot of illumination and the shorter the sampling time of sensor 305, the sampling frequency becomes higher.

Here, because of the natures of illumination optical system 100 and photo-detection unit 300, the waveform 802 is a function of the second power of linear Bessel function.

Figure 7A:
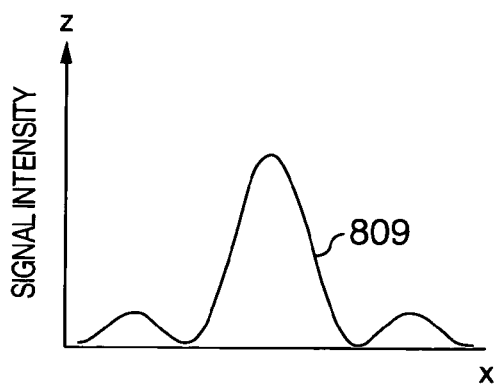
FIGS. 7A and 7B are graphs useful for comparison of a linear Bessel function with a Gaussian function.
Figure 7B:
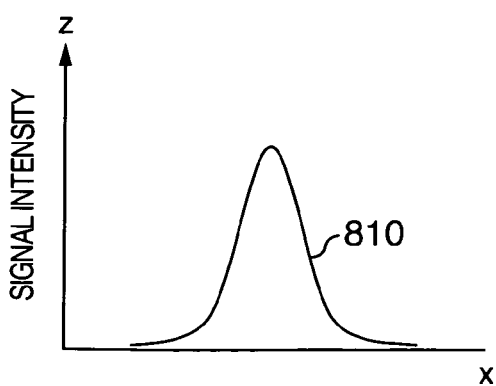

A function of the second power of linear Bessel function and a Gaussian function are illustrated in FIGS. 7A and 7B, respectively. Because of the analogy between the two functions, the waveform 802 can otherwise be approximated by the Gaussian function. In the following, a defect dimension measuring method will be studied on the assumption that the waveform 802 is approximated by using a Gaussian distribution. Depending on the size of a defect on the inspecting object 1, the width and height of the Gaussian distribution change. Further, the width and height of that distribution also change with the illumination intensity of the laser illumination the illumination optical system 100 uses. Accordingly, for various kinds of standard particles, the shape and characteristic quantity of detection waveforms are measured in advance using the apparatus construction of the present invention and a result of the measurement is compared with the detected waveform 802 to thereby obtain information about a size of a detected defect.

In a method for comparison of the waveform of a standard particle with the waveform 802 of a defect, a sum total (cumulative value) of signal intensities at a portion of defect data 801, that is, volume data of waveform 802 is measured and then volume data at the standard particle is compared with the volume data of defect data 801. But in case the illumination intensity of the illumination optical system 100 varies during the measurement of data, respective pieces of volume data are normalized by dividing them by illumination intensities of illumination optical system 100 used for them or the defect data 801 or volume data of the standard particle is multiplied by the ratio between illumination intensities in order for the volume data to be corrected.

Figures 8A, 8B, 8C:
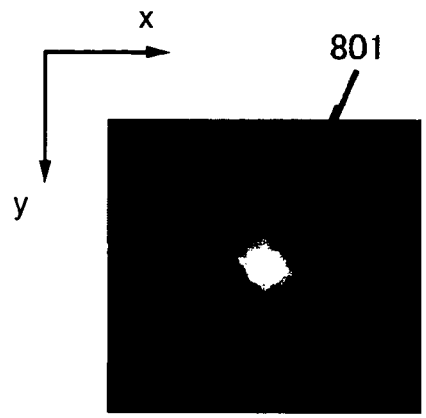
FIG. 8A is a diagram showing an image of a defect.
FIG. 8B is a diagram showing a distribution of variable density values of the image in FIG. 8A.
FIG. 8C is a diagram showing variable density values when noises are included.

In another method of comparing the waveforms, the maximum value of signal intensities of waveform 802 or the width of waveform 802 may be used for comparison. Apart from the volume data, the number of pixels on images of signals representative of the standard particle and the defect, respectively, may be used. This will be explained by making reference to FIGS. 8A to 8C. Like FIG. 5A, FIG. 8A illustrates an image of a defect, indicating defect data 801 representative of a signal of the defect attributable to rays of scattering light from the defect. In FIG. 8B, a variable density value of the defect data 801 is diagrammatically illustrated to show the defect signal indicated by a defect signal portion 811 contoured by a thick-line frame. In the case of an example shown in FIG. 8B, the aforementioned volume data corresponds to a sum total of variable density values of individual pixels, amounting up to 527. Then, the number of pixels on the image corresponds to the number of pixels inside the defect signal portion 811, amounting to 14 pixels and the width of the signal is 5 pixels in x direction and 5 pixels in y direction.

When the variable density values in FIG. 8B are affected by noises, they are changed as illustrated in FIG. 8C.

Figure 6A:
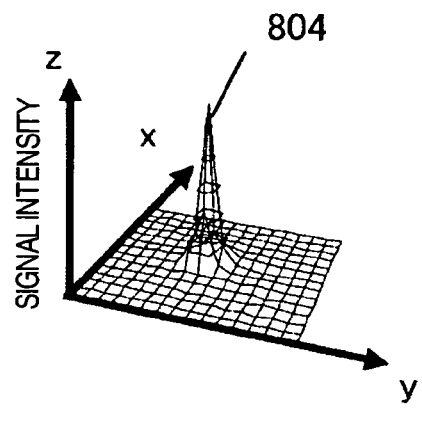
FIGS. 6A and 6C are diagrams for making contrast between two kinds of signal intensities.
Figure 6C:
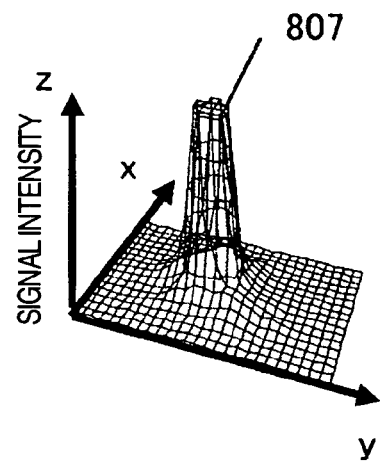

The method for determining the maximum value of signal intensities will now be described with reference to FIGS. 6A to 6D. Of these figures showing an example of waveform data representative of defect data like the waveform 802 shown in FIG. 5B, FIG. 6A illustrates an example where the signal waveform of defect data obtained by the photo-detection unit 300 is a cone-shaped waveform having a peak, which waveform demonstrates that the signal does not reach a saturation range of the sensor 305. FIG. 6C illustrates an example where the signal waveform of defect data is a waveform making a frustum top, which waveform demonstrates that the signal reaches the saturation range of the sensor 305 and data in excess of the saturation range do not exist, indicating a deficit.

Figure 6B:
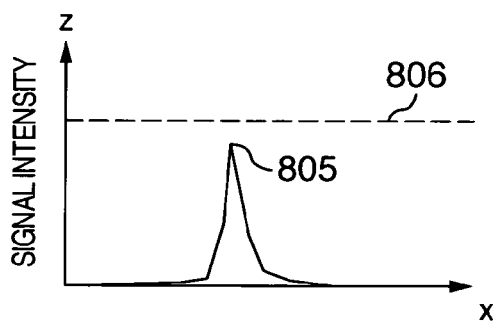
FIGS. 6B and 6D are diagrams for explaining determination of the maximum value of signal intensities.

In drawing the signal waveform as shown in FIG. 6A, the maximum value of signal intensities is set to a value which is maximal as a result of mutual comparison of signal intensities of individual pixels in the waveform, that is, to a peak point signal intensity 804 (or 805 in FIG. 6B). In drawing the signal waveform as shown in FIG. 6C, the maximum value of signal intensities is determined by performing calculation as below.

Figure 6D:
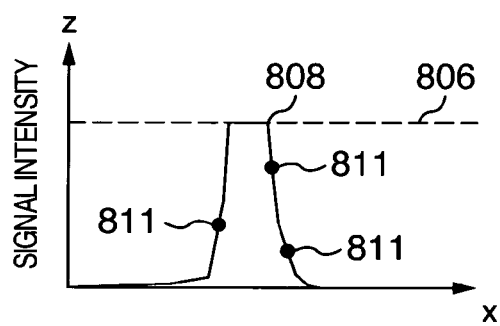

Firstly, in a saturation region 807, a maximum length standing upright on x-y plane of the saturated region is determined. The maximum length portion in FIG. 6C is sectioned on line parallel to x-axis to obtain a sectional waveform as shown in FIG. 6D. In FIG. 6D, abscissa represents a coordinate axis showing positions of pixels of the maximum length portion and ordinate is a coordinate axis showing the signal intensity. Signal intensity 808 indicates a saturation level of the sensor 305. In relation to this section, three or more points 811 are selected at which the signal is not saturated. Here, a description will be given on the assumption that 3 points are selected. More particularly, three points indicative of signal intensities of the unsaturated signal on the sectional waveform are selected in order of the magnitude. Where coordinates of the selected three points are x1, x2 and x3, respectively, and their signal intensities are z1, z2 and z3, respectively, equations of Gaussian distribution can be obtained for data of the selected three points by using unknowns k, σ and μ as follows:

$$z1 = k/\sigma \times \exp(-(x1-u)^2/(2\times\sigma^2))$$

$$z2 = k/\sigma \times \exp(-(x2-u)^2/(2\times\sigma^2))$$

$$z3 = k/\sigma \times \exp(-(x3-u)^2/(2\times\sigma^2))$$

The unknowns k, σ and μ can be determined by solving simultaneous equations of the above three equations.

Then, by using determined values of k and σ, the maximum value of the signal intensities in FIG. 6D can be calculated as being k/σ.

In the foregoing, the example of calculation using the unknown μ is explained but the use of the unknown μ is not always necessary. In such a case, two points of signal 811 are selected. Two points indicative of signal intensities of the unsaturated signal on the sectional waveform are selected in order of the magnitude. Where coordinates of the two selected points are x1 and x2, respectively, and their signal intensities are z1 and z2, respectively, equations of Gaussian distribution can be obtained for data of the two selected points by using unknowns k and σ as follows:

$$z1 = k/\sigma \times \exp(-(x1)^2/(2\times\sigma^2))$$

$$z2 = k/\sigma \times \exp(-(x2)^2/(2\times\sigma^2))$$

The unknowns k and σ can be determined by solving simultaneous equations of the above two equations and therefore, by using determined values of k and σ, the maximum value of the signal intensities in FIG. 6D can be calculated as being k/σ.

By determining in advance the maximum value of signal intensities obtained through the calculation as above in respect of a plurality of standard particles having different sizes, the relation between the size of a standard particle and the maximum value of signal intensities can be determined. By comparing the maximum value of signal intensities of an actually detected defect with the aforementioned correlation, the size of the defect can be determined.

Next, another embodiment when the maximum value of signal intensities is calculated will be described with reference to FIGS. 9A to 9C.

Figure 9A:
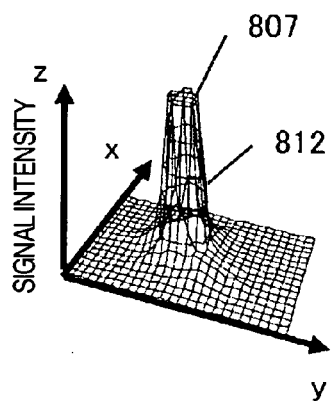
FIG. 9A is a graphic representation showing a distribution of saturated signal intensities on XY plane.
Figure 9B:
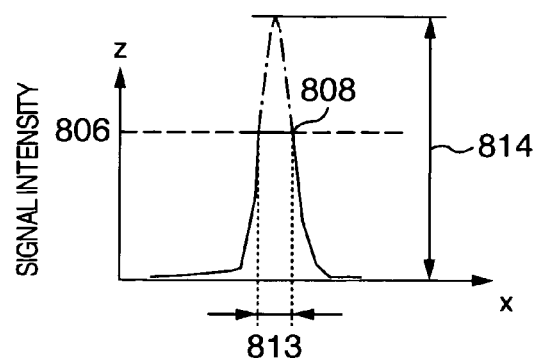
FIGS. 9B and 9C are a graph and a plan view for explaining how to determine the maximum value of signal intensities.
Figure 9C:
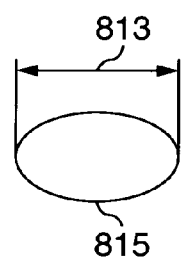

Of these figures, FIG. 9A illustrates a saturated signal distribution in which like FIG. 6C the signal waveform of defect data is a frustum-shaped waveform and FIGS. 9B and 9C are diagrams showing the shape of the saturated signal portion and being useful to explain determination of the maximum value of signal intensities.

The relation between a signal waveform 812 and a top portion 807 is illustrated in FIG. 9A and of the signal waveform 812, a portion reaching the saturation region of the sensor 305 to lack data in excess of the saturation region is at the top 807.

A sectional waveform of the signal waveform 812 is illustrated in FIG. 9B and in the figure, ordinate represents the signal intensity and abscissa represents the position of pixels of the signal. A saturation level 806 indicates the saturation level of the sensor 305 and a signal width 813 indicates the width of the top 807. Signal intensity 814 is a maximum value which would be obtained with an unsaturated sensor.

Next, a method of calculating the maximum value 814 of signal intensities from the saturated signal waveform 812 will be described. Where the saturation level 806 is SL, the signal width 813 is SW and the signal intensity 814 is PL, $$SL = k/\sigma \times \exp(-(-SW/2)^2/(2\times\sigma^2))$$

$$PL = k/\sigma$$

can be obtained through approximation based on Gaussian distribution. In the equations, k is a coefficient and σ is a value which can be calculated from the construction of the optical system in the defect inspection apparatus of the present invention.

Accordingly, from the two equations as above, PL can be calculated as $$PL = SL/\exp(-(-SW/2)^2/(2\times\sigma^2))$$

where the SL is an output when the sensor 305 is saturated and for example, when an AD converter of the photo-detection unit 300 is of 8 bits, the SL is of 255 gradation. Depending on the construction of the optical system, the σ is given values of 0 to 1. Subsequently, a method for calculation of SW will be described.

Illustrated in FIG. 9C is the shape of top 807. In this region, the photo-detection unit 104 is saturated. In the figure, an saturation area 815 and the signal width 813 are shown. Since the signal waveform 812 is deemed as complying with the Gaussian distribution, the shape of saturation area 815 can be supposed to be circular. Therefore, where the signal width 813 is SW and the saturation area has an area of SA, $$SW = 2\times\sqrt{(SA/\pi)}$$

can be calculated. It is to be noted that √(A) signifies calculation of a square root of A and it is the circle ratio. The area of saturation area 815 corresponds to the number of pixels for which the sensor 305 is saturated. In connection with the saturated pixels, the maximum value of output of the AD converter of sensor 305 can be used which is set in consideration of electrical noise of the sensor 305. For example, when the AD converter is of 8 bits, the maximum value of output is of 255 gradation but when the electrical noise is of 10 gradation, saturation may be considered as taking place for 245 or more gradation.

If the signal waveform 807 is not saturated, calculation similar to the above may be carried out by using the maximum value of signal waveform 807 as saturation level 806.

Through the above calculation, the maximum value of signal intensities can be calculated and therefore, by comparing a value calculated with a standard particle with a value detected with a detected defect, the size of the defect can be measured.

Figure 10A:
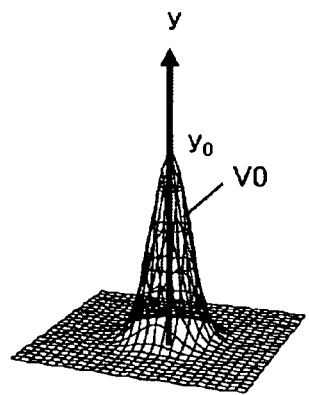
FIGS. 10A, 10B and 10C are diagrams showing signal waveforms of defects, with FIGS. 10B and 10C especially illustrating signal intensity cumulated values of a signal intensity portion for which the signal intensity is smaller than different specified values.
Figure 10B:
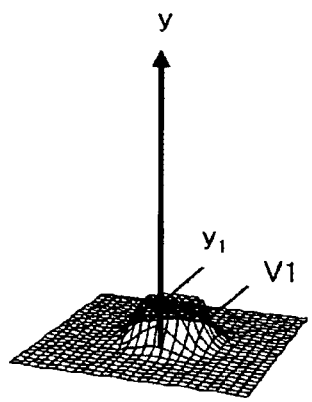
Figure 10C:
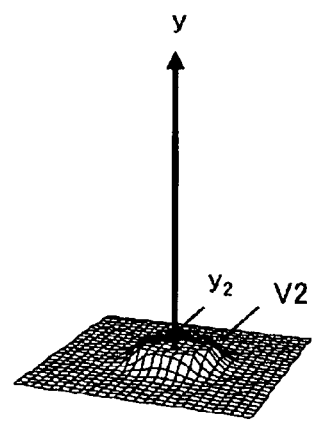

While the foregoing description is given by taking the maximum value of signal intensities, for instance, a cumulative value of signal intensities of a defect may be used in place of the maximum value of signal intensities. In this case, in a method of calculating a cumulative value of signal intensities of the defect, a value obtained by adding variable-densities of individual pixels of a detected defect may be used. The use of the cumulative value has an advantage that the error in sampling signals can be reduced. Here, a signal intensity correction method using a cumulative value of signal intensities will be described. Referring to FIGS. 10A to 10C, the Gaussian distribution is expressed three-dimensionally. FIG. 10A shows an instance where detection is performed by means of a sensor with which the defect signal is not saturated, FIG. 10B shows that the signal is saturated at $y=y_1$ and FIG. 10C shows signals less than $y=y_2$ ($<y_1$). In the method to be described below, signal intensities covering the entire Gaussian distribution can be calculated when cumulative values of signal intensities can be obtained in connection with FIGS. 10B and 10C.

It is assumed that the volume of the entire Gaussian distribution is $V0$ and the maximum value of signal y is $y_0$ in FIG. 10A, the volume of a portion below $y=y_1$ is $V1$ in FIG. 10B and the volume of a portion below $y=y_2$ ($<y_1$) is $V2$ in FIG. 10C. With the sectional shape of Gaussian distribution taken on line parallel to x-axis in FIG. 9B, the sectional shape is supposedly expressed by $$y = y_0 \cdot \exp(-x^2/2/\sigma^2)$$

In this condition, when integration is taken along y-axis and the Gaussian distribution is sectioned orthogonally to y-axis at arbitrary two points a and b on y-axis (where $0 \leq a \leq b \leq y_0$), a volume $V_{a\sim b}$ of Gaussian distribution between the points a and b can be expressed by the following equation:

$$V_{a-b} = 2\pi \cdot \sigma^2 [b \cdot \{\text{Log}(y_0) - \text{Log}(b)\} - a \cdot \{\text{Log}(y_0) - \text{Log}(a)\} + (b-a)]$$

Accordingly, by substituting $(0, y_0)$ for $(a, b)$, $V0$ can be expressed as follows:

$$V0 = 2\pi\sigma^2 \cdot y_0$$

Then, by substituting $(0, y_1)$ for $(a, b)$ and $(0, y_2)$ for $(a, b)$, $V1$ and $V2$ can be expressed as follows:

$$V1 = 2\pi\sigma^2 \cdot y_0 \cdot [y_1 \cdot \{\text{Log}(y_0) - \text{Log}(y_1)\} - y_1]$$

$$V2 = 2\pi\sigma^2 \cdot y_0 \cdot [y_2 \cdot \{\text{Log}(y_0) - \text{Log}(y_2)\} - y_2]$$

In the above equations "Log" signifies calculation of natural logarithm. By rewriting a volume ratio $V1/V2$ to CC, the CC can be calculated as follows:

$$CC = [y_1 \cdot \{\text{Log}(y_0) - \text{Log}(y_1)\} - y_1] / [y_2 \cdot \{\text{Log}(y_0) - \text{Log}(y_2)\} - y_2]$$

When considering that $y_1$ and $y_2$ are values smaller than the saturation level of the sensor 305 and hence $V1$ and $V2$ can be measurable, the above equation is an equation of one variable concerning the variable $y_0$ and therefore can be solved for $y_0$. With $y_0$ determined, $\sigma$ can be determined from equation for determination of $V1$ or $V2$. Since $y_0$ and $\sigma$ are determined in this manner, the entire volume $V0$ of the Gaussian distribution can be calculated.

The present invention has been described as using the AD converter of 8 bits but an AD converter of 10 bits or more may be used. The larger number of bits is meritorious in that changes in intensity of light obtained by the photo-detection unit can be acquired finely and therefore a defect or the size of the defect can be calculated with high precision. Further, the present invention has been described by taking an instance where the signal waveform of a defect is approximated by a Gaussian distribution but even when a function resulting from approximation using two variables other than the Gaussian distribution is used, a cumulative value of signal intensities can be obtained through a method similar to the aforementioned method. In the case of three or more variables, volumes $V3, V4, \ldots$ for signal values less than an arbitrary value below the saturation level can be used in addition to the volumes $V1$ and $V2$ so that variables necessary for calculation of the cumulative value of signals may be determined.

To add, in the present embodiment, the illumination optical system 100 has been exemplified as using the laser beam in describing the construction of the apparatus but white light may be used instead of the laser beam. If the inspecting object is a circuit pattern having a repeat nature, the difference between an image having no defect on the repeat pattern and an image having a defect thereon may first be acquired and thereafter, the previously-described size measurement process may be carried out. Further, in case a defect is present on a circuit pattern or a film, for example, an oxide film or metal film and, irrespective of the presence or absence of the repeat nature, data of rays of scattering light or reflection factor data is acquired in advance from the circuit pattern or the film, the size data of the defect may be corrected by using that data. Furthermore, in the present example, comparison with the size of a standard particle for the purpose of measuring the size of a defect has been described but comparison with a defect of known size substituting for a standard particle may be adopted.

Figure 11:
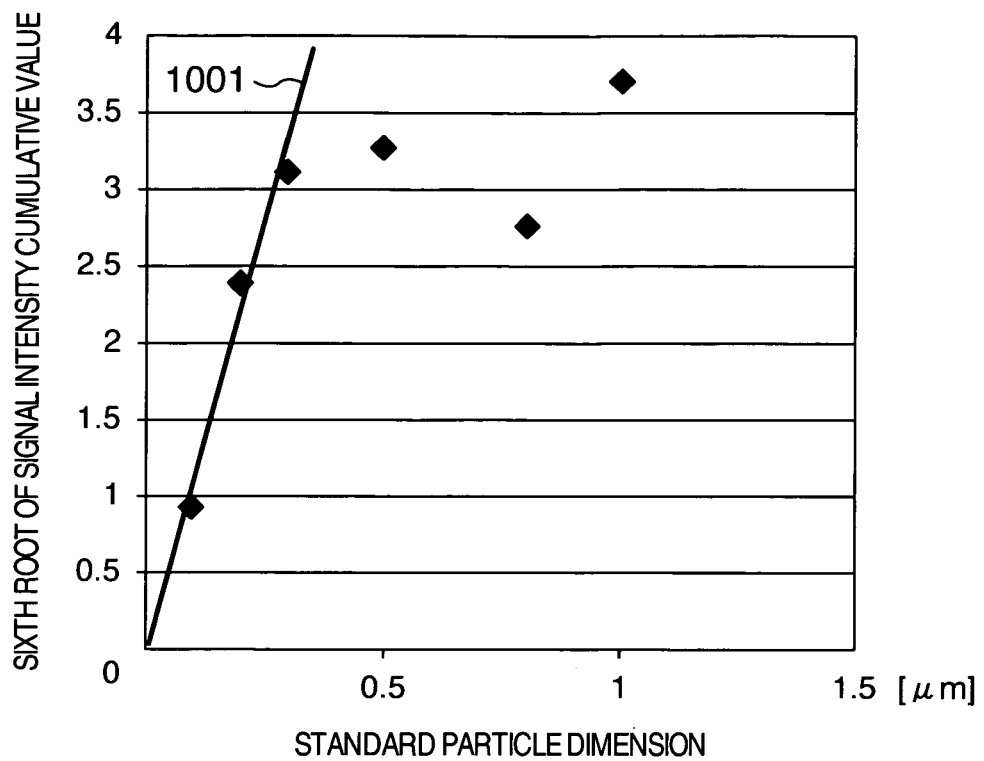
FIG. 11 is a graph showing the relation between the size of standard particles and the sixth root of the signal intensity cumulative value.

The cumulative value of signals thus determined is converted into a size according to a method to be described hereinafter. When the particle size of a particle is smaller than the wavelength as described previously, it is known that the Rayleigh scattering theory stands and the quantity of scattering light is proportional to the sixth power of the particle diameter. Therefore, by determining the sixth root of the cumulative value and by multiplying it by a proportional coefficient complying with the intensity of illumination, the conversion to the dimension can be achieved. FIG. 11 is a graph showing data obtained when a mirror wafer of silicon (Si) coated with standard particles is inspected with the defect inspection apparatus. In the graph, abscissa represents the dimension of standard particle and ordinate represents the sixth root of the signal intensity cumulative value. The data is obtained at the illumination wavelength being about 0.5 μm and therefore validity of the good proportional relation between the particle diameter and the sixth root of the signal intensity cumulative value can be seen clearly for standard particles of 0.1 μm, 0.2 μm and 0.3 μm particle diameters which are smaller than the wavelength. An approximate curve 1001 is calculated through the method of least squares on the basis of data of standard particles of 0.3 μm or less particle diameters. At that time, when representation of abscissa is substituted for x and representation of ordinate is substituted for y in the graph, the approximate curve can be expressed by equation y=a×x+b, where a and b are values determined through the method of least squares. Then, for calculation of defect dimension x from the sixth root y of the signal cumulative value, x=(y−b)/a may be computed.

Figure 13:
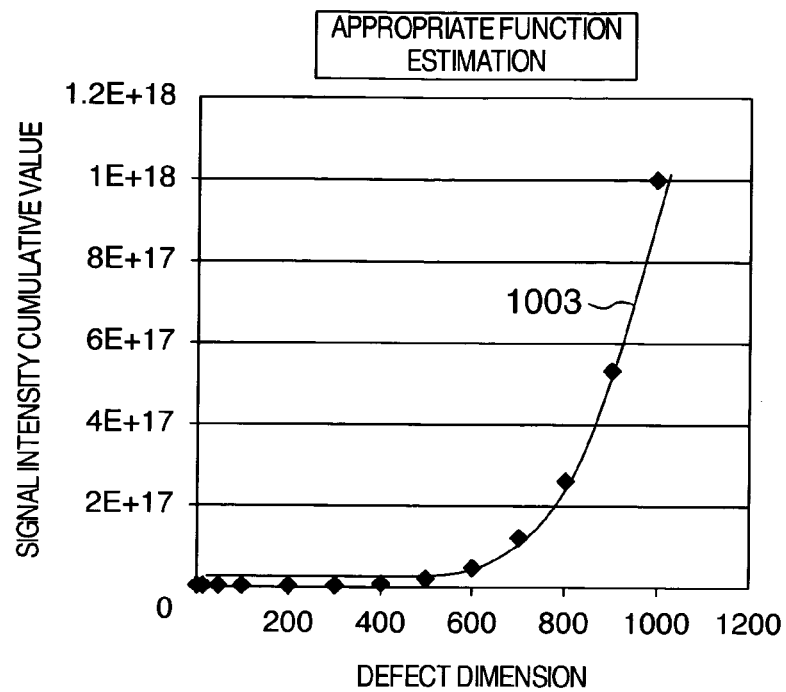
FIG. 13 is a graph showing the relation between the size of standard particles and the cumulative value of signal intensities.

Turning now to FIG. 13, there is illustrated a graph showing the relation between defect dimension and cumulative value of signals. Since according to the Rayleigh scattering theory the sixth power of the dimension is proportional to the cumulative value of signals, an approximate curve is determined exemplarily on the basis of this relation.

Figure 14:
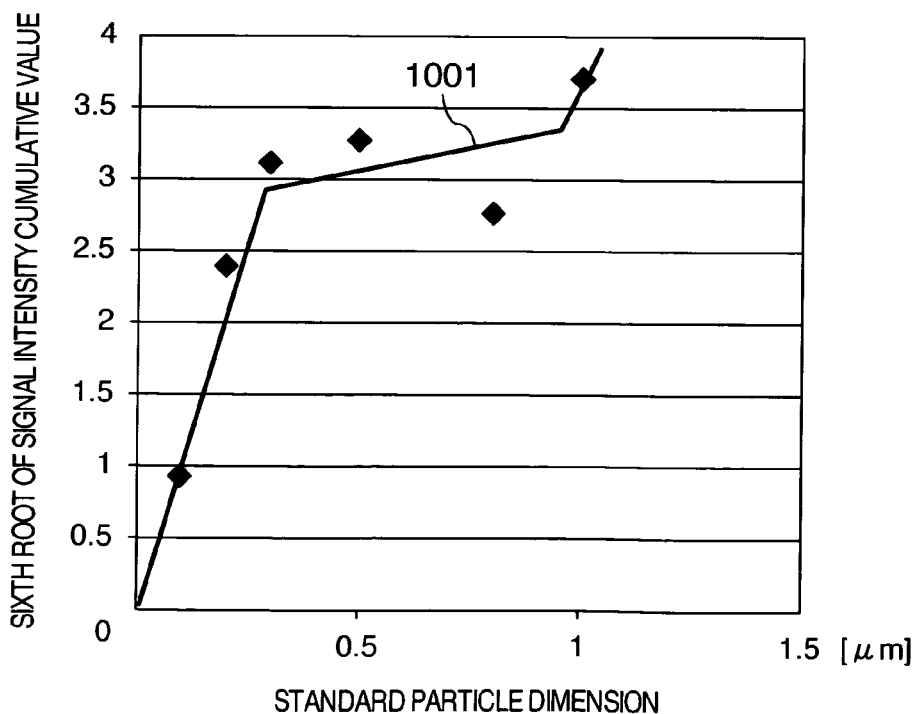
FIG. 14 is a graph showing an example where approximate curves differing with the size are applied.

In the case of an example of graph shown in FIG. 14, a plurality of conversion expressions are provided for conversion of the cumulative value of signals to the dimension. As well known in the art, when the dimension of a particle is smaller than the wavelength, the Rayleigh scattering theory stands whereas the Lorentz Mie theory stands for the particle dimension nearly equaling the wavelength and the approximation of Fraunhofer stands for the particle dimension being sufficiently larger than the wavelength. Accordingly, the relation between signal cumulative value and dimension can be provided differently depending on the particle dimension, thus improving the accuracy of dimension calculation.

In the present embodiment, an example has been described in which the wafer coated with standard particles is measured in determining the approximate curve but in another embodiment, a standard wafer built in with patterns and defects of known dimensions may also be used. Further, due to the fact that scattering from a particle is affected by a reflection factor of the wafer surface, either a wafer formed with a film of a material used during semiconductor production or a sample of a wafer of actual product coated with standard particles may be adopted in place of the mirror wafer. In this case, by adaptively using optimum approximate curves for individual inspection steps, highly accurate dimension measurement can be achieved.

In still another embodiment, the quantities of scattering light by particles are calculated in advance through simulation and stored in the form of a database so that a suitable approximate curve may be selected during an inspection in accordance with a production step and a material of wafer surface. In this case, since the signal intensity to be detected changes with the illumination intensity constituting the inspection condition, the quantity of scattering light corresponding to at least one illumination intensity is measured in advance. If an inspection proceeds at an illumination intensity N times the illumination intensity measured in advance, simulation data of the scattering light quantity may be N multiplied. Available as a simulator for calculation of the quantity of scattering light from a particle is an MIST by NIST (National Institute of Standards and Technology), an EMF lex by Weidlinger Associates, Inc., or DDSURF by Laser Diagnostics Laboratory of Arizona State University.

Figure 12:
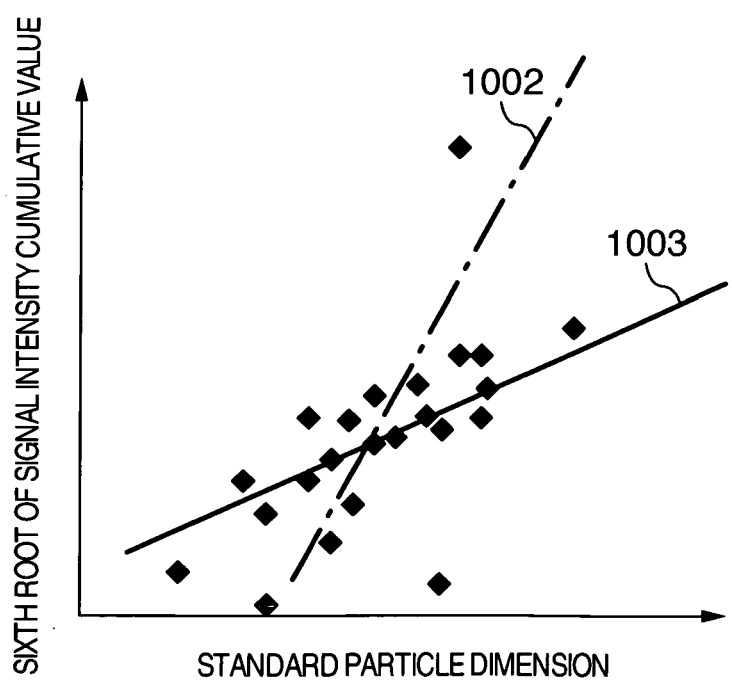
FIG. 12 is a graph showing examples of calculation of approximate curves based on the method of least squares and the M-estimation method, respectively.

Although the method of least squares has come up exemplarily in connection with the method of determining the approximate curve but the method of least squares has a nature susceptible to the influence of the outlying value. Therefore, a robust estimation method immune to the influence of the outlying value may be adopted. A description will be given by way of example of an M-estimation. In the method of least squares, where the error between an i-th sample and an approximate curve is Ei, an evaluation criterion as expressed by the following equation:

$$LMS = \min \Sigma (Ei)^2$$

is used. According to this evaluation criterion, when the error between a model and a sample complies with a standard deviation of average 0, an estimated model is optimized. But in case the sample contains an outlying value, a good model cannot always be estimated. Under the circumstances, the M-estimation comes up in which the aforementioned evaluation criterion is so modified as to give a small weight to an outlying value. FIG. 12 is illustrative of comparison of the method of least squares with the M-estimation. An approximate curve 1002 is based on the method of least squares and an approximate curve 1003 is based on the M-estimation. Where a weight function distant by d from a model is w(d), the evaluation criterion based on the M-estimation is expressed by the following equation:

$$M = \min \Sigma \{w(d) \cdot Ei^2\}$$

Figure 15:
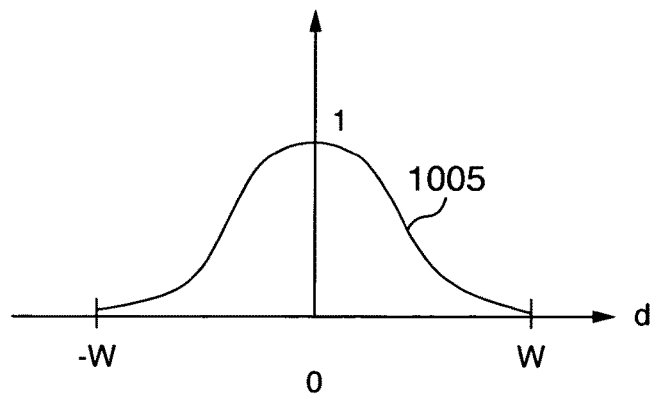
FIG. 15 is a graph showing an example of weight function in the M-estimation method.

FIG. 15 illustrates an example of weight function which is expressed by the following equation:

$$w(d) = \begin{cases} \{1-(d/W)^2\}^2 & \dots \ |d| \leq W \\ 0 & \dots \ |d| > W \end{cases}$$

Since, pursuant to the above weight function w(d), the influence of a sample distant from the model by more than W is not considered, the immunity to the influence of the outlying value can be assured.

Figure 16:
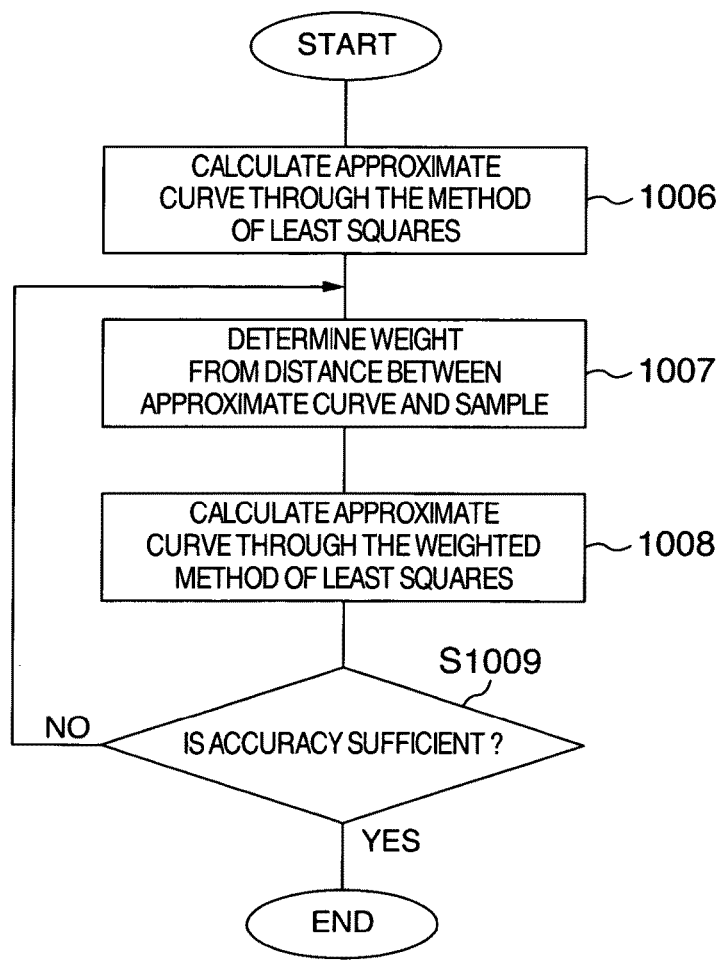
FIG. 16 is a flowchart showing the procedures for data processing in the M-estimation method.

Turning to FIG. 16, there is shown a flowchart of determining an approximate curve pursuant to the M-estimation. At the outset, an initial value is determined in step 1006 through the method of least squares. In step 1007, a weight is determined from a distance between the approximate curve and a sample in accordance with a weight function w (d). In step 1008, a method of weighted least squares is executed to calculate the approximate curve. It is decided in step 1009 whether the accuracy of the approximate curve is sufficient and if the accuracy is determined to be insufficient, the steps 1007, 1008 and 1009 are repeated.

Available as another method for determination of an approximate curve is LMS-estimation or LTS-estimation. In the LMS-estimation, a median of a square of the difference between the model and a sample is minimized. In the LTS-estimation, for n samples, squares of errors each between the model and each of the n samples are arrayed in order of smaller to larger values and the sum of squares of errors up to an {h (n/2)+1}-th square of error is minimized.

By combining the method of least squares with the robust estimation in this manner, the immunity to the influence of outlying value can be achieved, thereby ensuring that the relation between the signal intensity and the particle diameter can be determined properly.

In the foregoing description, a defect inspection is executed by using rays of scattering light. This method is meritorious in that a defect can be found highly efficiently. Determining the size of a detect according to the aforementioned method leads to an advantage that the defect can be found without resort to a particular light source dedicated to measurement of the size and that the measurement of the size can be accomplished with a light source resulting from the same rays of scattering light.

[As Regards Defect Signal Estimation and Sampling when the Defect Signal is Saturated]

Figure 17:
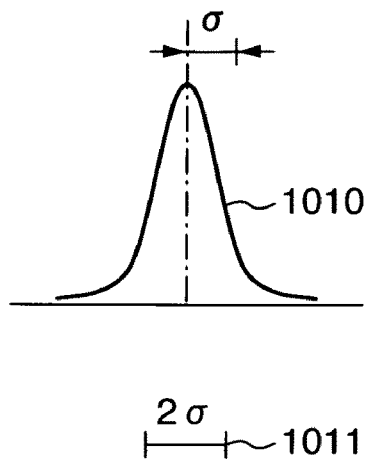
FIG. 17 is a graphic representation showing the relation between the Gaussian function and the sampling pitch.
Figure 18:
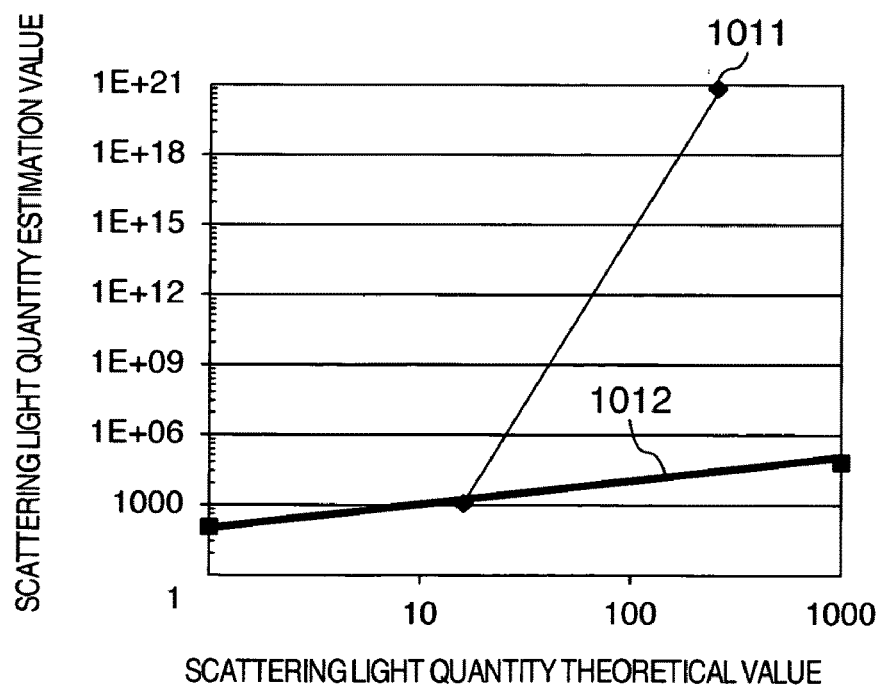
FIG. 18 is a graph useful to compare the relation between the theoretical value of scattering light quantity and the scattering light quantity estimative value from the standpoint of the sampling pitch.
Figure 19:
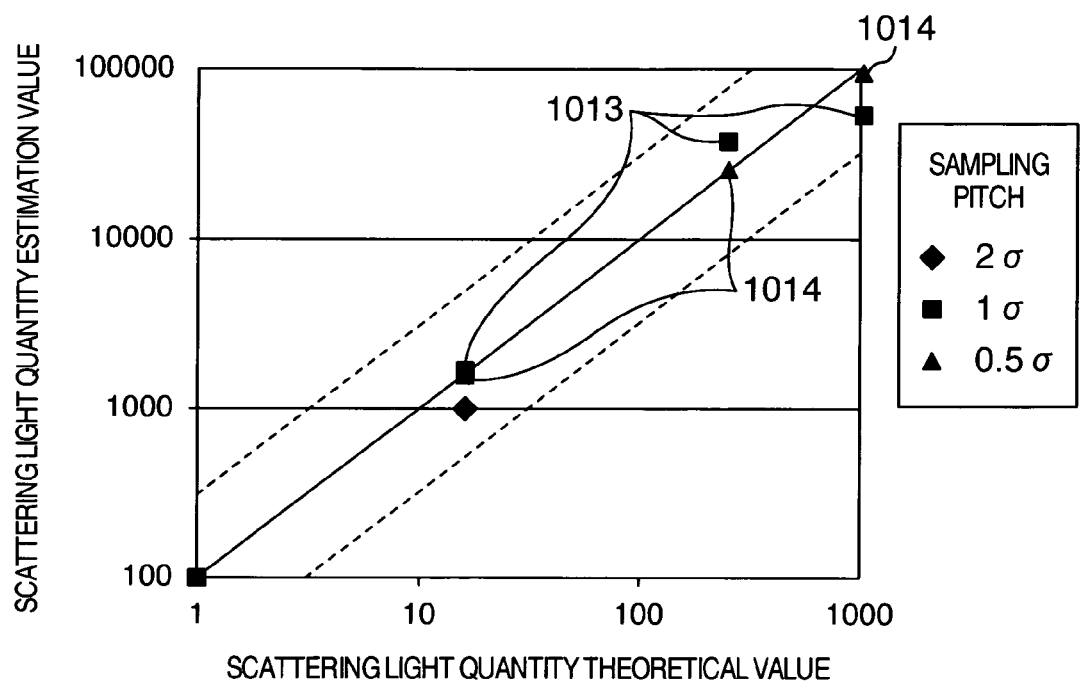
FIG. 19 is a graph similar to FIG. 18.

The relation between the signal waveform of a defect and the sampling pitch is illustrated in FIG. 17. A waveform 1010 is a signal waveform of a defect which is approximated by a Gaussian function. A sampling pitch 1011 shows an instance where the sampling pitch during defect detection is 2σ. The theoretical value of signal intensity cumulative value as the illumination intensity increases and errors occurring in the estimation of the signal intensity cumulative value based on the method explained in connection with FIG. 16 are shown in FIGS. 18 and 19 in respect of different sampling pitches. Data in FIG. 18 is obtained for a sampling pitch being 2σ as indicated at plotting 1011 and it is demonstrated that as the illumination intensity increases by 100 times or more, the error becomes very large. In FIG. 19, part of FIG. 18 is illustrated exaggeratedly. In a zone bounded by dotted line, the dimension accuracy is within ±20%. Plotting 1013 for the sampling pitch being 1σ and plotting 1014 for the sampling pitch being 0.5σ are both realized within the accuracy ±20%. Because of the analogy between the linear Bessel function and the Gaussian function, 2σ in the Gaussian function is deemed to correspond to the resolution of the photo-detection unit 300. From FIGS. 18 and 19, it will be seen that even when defects responsible for generation of rays of scattering light which differ by 3 figures in the quantity of light are present on the same wafer, the signal waveform needs to be sampled at a pitch half or less the resolution of the photo-detection unit 300 in order to calculate the dimension with high accuracies.

[Correcting Optical System for Aberration and Sensor for Irregularities in Sensitivity]

Figure 20A:
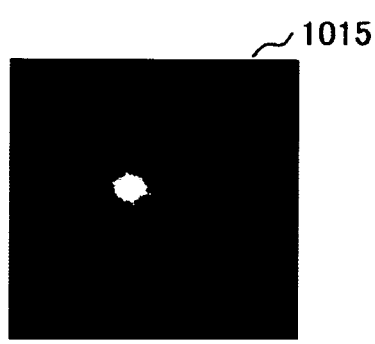
FIGS. 20A and 20B are diagrams for explaining aberration in the optical system.
Figure 20B:
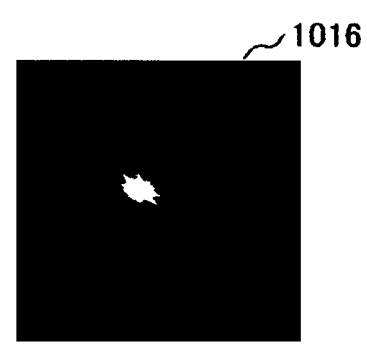

In the foregoing embodiments, aberration of the optical system and irregularities in sensitivity of the sensor have not been referred to but in the actual inspection apparatus, these factors will have the influence upon the accuracy of dimension calculation. In an embodiment in which the photo-detection unit 300 uses an image forming optical system, the aberration behaves in the center of detection view field and at the periphery of the detection view field as illustrated in FIGS. 20A and 20B. In the figures, detected images obtained when a wafer coated with standard particles of the same dimension is measured are shown, providing a defect detection image in the center of the view field in FIG. 20A and a defect detection image at the periphery of the view field in FIG. 20B. Two methods for relieving the influence of aberration can be considered, of which one is for measuring the degree of aberration in advance and providing a correction table or correction expression based on the measurement result and the other is for proceeding with relief on real time base during an inspection. In describing the embodiment in connection with FIGS. 10A to 10C, it has already been shown that even if how far the detection signal spreads is unknown, the quantity of scattering light can be calculated properly.

Figure 21A:
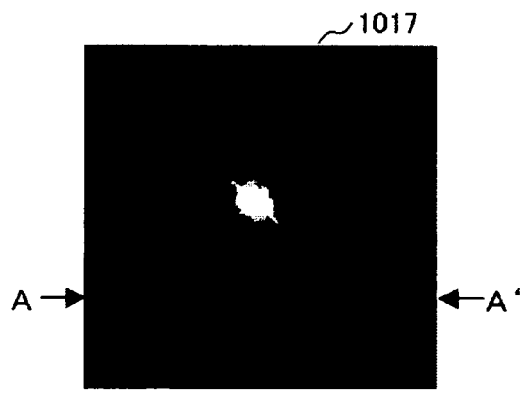
FIGS. 21A and 21B are diagrams for explaining irregularities in sensitivity of a sensor which depend on the pixel.
Figure 21B:
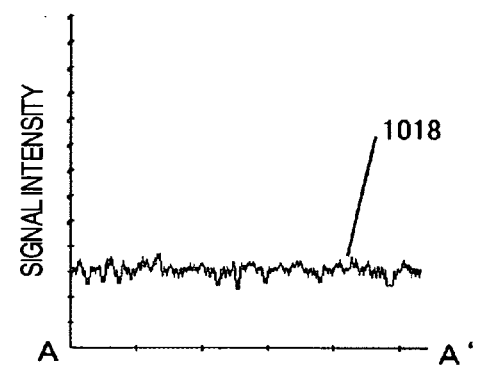

Reference will now be made to FIGS. 21A and 21B illustrating irregularities in sensitivity of the sensor 305. Of these figures, FIG. 21A depicts image data of a detected defect and FIG. 21B shows a signal waveform taken on A-A' section in FIG. 21A. Since in the Rayleigh scattering region the defect dimension is proportional to the sixth root of the quantity of scattering light, the irregularity of the degree approximating that shown in FIG. 21B is found not to be a factor of reducing the accuracy of dimension calculation.

Figure 22A:
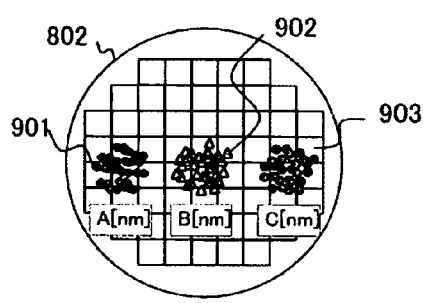
FIGS. 22A to 22C are diagrams for explaining an example of a dimension correction method using standard samples.
Figure 22B:
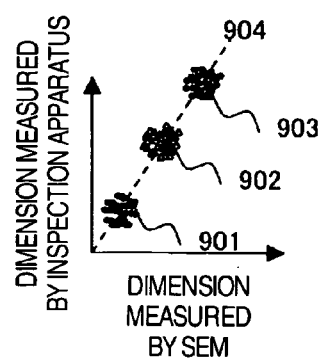
Figure 22C:
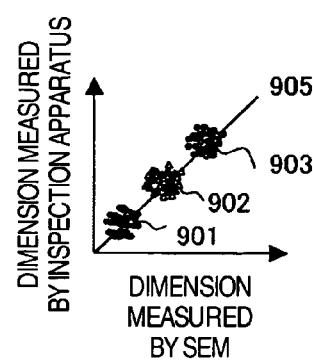

By making reference to FIGS. 22A to 22B, an example of dimension correction using a wafer provided with standard samples will be described. This example has the relation to the step S140 in FIG. 1. A plural kinds of standard particles of known dimension are scattered as shown in FIG. 22A. The relation between the dimension measured with the SEM before correction and the dimension measured with the inspection apparatus is illustrated in FIG. 22B and the relation between the dimension measured with the SEM after correction and the dimension measured with the inspection apparatus is illustrated in FIG. 22C.

The correction proceeds as will be described below. When the wafer provided with the standard samples shown in FIG. 22A is inspected with the inspection apparatus and the dimension is calculated, the dimension will not sometimes be determined correctly owing to, for example, irregularities in manufacture of constituent components of the apparatus. The standard sample is known in dimension and therefore, by comparing the apparatus output with the true value and expressing the correlation by an approximate expression, correction can be made. For determination of the approximate expression, the method of least squares or the robust estimation method may be used. By determining the approximate expression and making the correction, the dimension can be determined highly accurately as illustrated in FIG. 22C.

Figure 23A:
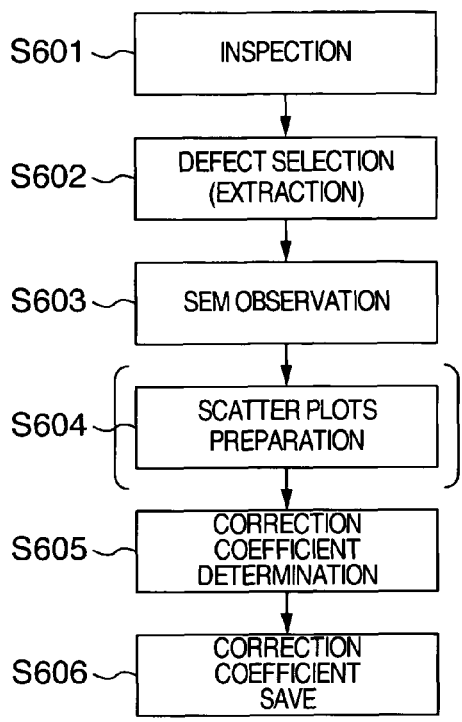
FIGS. 23A and 23B are flowcharts showing examples of the procedures in a dimension correction method.
Figure 23B:
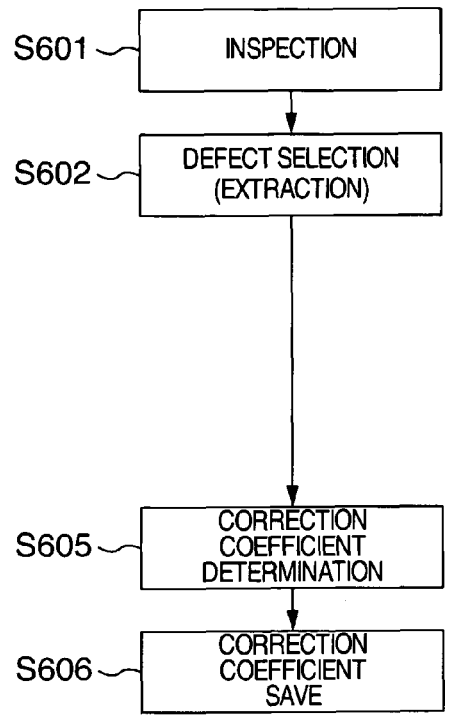

In FIGS. 23A and 23B, the procedures for correcting or correcting the defect dimension are shown. A flowchart in FIG. 23A is applied to an example of a defect of unknown dimension so that a correction coefficient may be calculated by using, for example, a defect on an actual product wafer. Since defects on the product wafer are unknown in dimension, the dimension of each defect needs to be measured by using an observation apparatus such as the SEM. A flowchart in FIG. 23B is applied to an example where a correction coefficient is calculated by using a defect of known dimension. In the foregoing description given in connection with FIGS. 22A to 22C, the standard particle is taken as an example of the sample of known dimension but alternatively, a defect controlled for its dimension may be formed on the wafer through photolithography or FIB.

Figure 24:
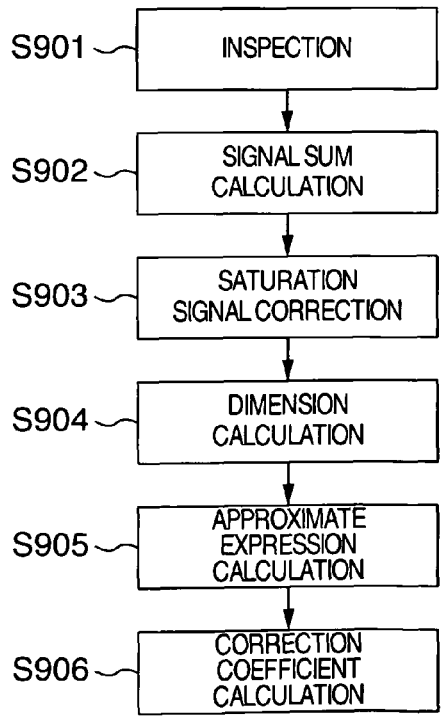
FIG. 24 is a flowchart showing the procedures for calculation of correction coefficients.

An example of a flowchart of calculating a dimension correction coefficient is shown in FIG. 24.

Reverting again to FIG. 1, another embodiment will be described.

To handling the step S110, the detection technique using the dark field illumination and the image forming optical system in combination in FIG. 2 has been exemplified previously but another method may be employed, provided that it can detect rays of light from a defect or pattern. For example, a detection system using the bright field illumination and the image forming optical system or using the dark field illumination and the focusing optical system may be adopted.

To handle the step S120, the difference in images may be acquired between adjacent dies during extraction of a defect region and by setting a suitable threshold value, the defect region may be extracted.

Figure 25A:
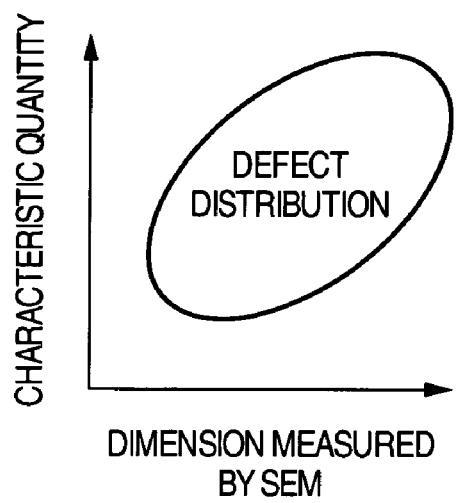
FIGS. 25A and 25B are graphic representations showing an example where calculation of the characteristic quantity related to the dimension is executed case by case in compliance with sorting by characteristic quantities and other kinds of information.
Figure 25B:
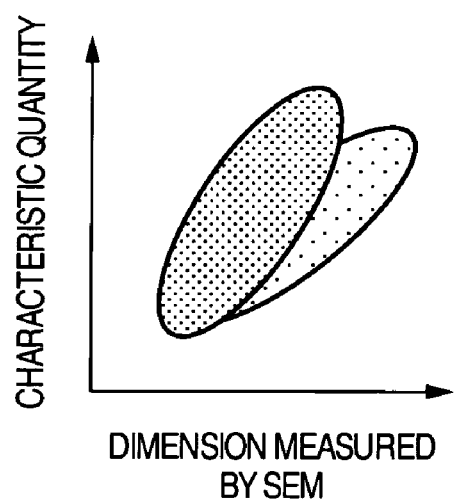

To handle the step S130, other characteristic quantities than the quantity of scattering light and the maximum value of signal intensities may be used as the quantity characteristic of a defect. In that case, information about coordinate data and adjoining dies can be reflected on calculation of the characteristic quantity. Also, the inspection condition of the inspection apparatus may be reflected. For example, the inspection condition includes the wavelength, light quantity and incident angle of the illumination, the scanning speed of the stage and the magnification and numerical aperture of the photo-detection unit. Information about irregularities in manufacture of the inspection apparatus per se may be reflected. The manufacturing irregularities include the irregularity in quantity of illumination light, the aberration of lens and the irregularity in sensitivity of the sensor. Two methods of reflecting data are available, of which one is a method of incorporating the data as a variable into the characteristic quantity calculation expression and the other is a method of sorting cases on the basis of the information and proceeding with the cases independently. In the first method, after calculation of the characteristic quantity, the program proceeds directly to the step 140. FIGS. 25A and 25B are useful to explain an example of sorting cases according to the second method. Illustrated in FIG. 25A is a graph showing the relation between the SEM measurement dimension and the characteristic quantity concerning the dimension. Illustrated in FIG. 25B is a graph showing an example where cases are sorted on the basis of the characteristic quantity, the inspection condition and manufacturing irregularity information of the inspection apparatus per se. By virtue of the case by case sorting, irregularities in individual groups resulting from sorting can be reduced. The step S130 is followed by branching steps based on the case by case sorting and each branching step continues to the step S140 in which the relation between the dimension and the signal cumulative value is determined to calculate the dimension.

[As Regards Optical System of Defect Inspection Apparatus]

In the foregoing description of this invention, the optical system of the defect inspection system has been described as detecting a defect by using rays of scattering light and measuring the size of the defect but the method of this invention can also be applicable to an optical system for detecting a defect by using rays of reflection light and measuring the size of the defect. Generally, the use of the scattering light enjoys high efficiency of inspection but is bad at accuracy of measurement whereas the use of the reflection light is bad at efficiency of inspection but good at accuracy of measurement. The method of the present invention can be applicable to the both cases.

As has been set forth so far, according to the present invention, a defect inspection apparatus and a defect inspection method can be provided which can speedily proceed with countermeasures against faults in execution of the inspection of production process of semiconductor wafer and thin film substrate and in the faulty analysis as well by measuring the size of a defect or of a pattern defect with high accuracies.

The invention may be embodied in other specific forms without departing from the spirit or essential characteristics thereof. The present embodiment is therefore to be considered in all respects as illustrative and not restrictive, the scope of the invention being indicated by the appended claims rather than by the foregoing description and all changes which come within the meaning and range of equivalency of the claims are therefore intended to be embraced therein.

The invention claimed is:

1. A defect inspection apparatus for inspecting defects on an inspecting object, comprising:
   illumination means for irradiating a beam of light on said inspecting object;
   photo-detection means for detecting rays of light given off from said inspecting object under the irradiation of the light beam by said illumination means;
   defect detection means for detecting a defect by processing a signal obtained through detection by said photo-detection means;
   characteristic quantity calculation means for calculating a characteristic quantity related to a size of the defect; and
   defect size correction means for correcting the size of the detected defect by using a ratio between the calculated characteristic quantity of the characteristic quantity calculation means and a corresponding characteristic quantity of a standard particle measured and calculated in advance.

2. A defect inspection apparatus according to claim 1, wherein said calculated characteristic quantity is the sum total of intensities of said signal.

3. A defect inspection apparatus according to claim 1, wherein said calculated characteristic quantity is the maximum value of intensities of said signal.

4. A defect inspection apparatus according to claim 1, wherein said photo-detection means has a sampling pitch which is half or less the optical resolution.

5. A defect inspection apparatus according to claim 1, wherein in a process for determining the size of a defect, parameters inherent of the inspection apparatus are used.

6. A defect inspection method for detecting defects on an inspecting object comprising:
   illumination step of irradiating a beam of light on said inspecting object;
   photo-detection step of detecting rays of light given off from said inspecting object under the irradiation of the light beam in the illumination step;
   defect detection step of detecting a defect by processing a signal obtained through detection in the photo-detection step;
   characteristic quantity calculation step of calculating a characteristic quantity related to a sizes of the defect; and
   defect size correction step of correcting the size of the detected defect by using a ratio between the calculated characteristic quantity of the characteristic quantity calculation step and a corresponding characteristic quantity of a standard particle measured and calculated in advance.

7. A defect inspection method according to claim 6, wherein as said calculated characteristic quantity, the sum total of intensities of said signal is used.

8. A defect inspection method according to claim 6, wherein as said calculated characteristic quantity, the maximum value of intensities of said signal is used.

9. A defect inspection method according to claim 6, wherein said photo-detection step is executed at a sampling pitch which is half or less the optical resolution.

10. A defect inspection method according to claim 6, wherein in a process for determining the size of a defect, parameters inherent of an inspection apparatus are used.

* * * * *